(12) United States Patent
Huebler et al.

(10) Patent No.: US 8,156,810 B2
(45) Date of Patent: Apr. 17, 2012

(54) METHOD FOR IDENTIFYING DEFECTIVE HEAT FUSION JOINTS

(75) Inventors: James Emerson Huebler, Brookfield, IL (US); Maurice Givens, Chicago, IL (US)

(73) Assignee: Gas Technology Institute, Des Plaines, IL (US)

( * ) Notice: Subject to any disclaimer, the term of this patent is extended or adjusted under 35 U.S.C. 154(b) by 374 days.

(21) Appl. No.: 12/644,056

(22) Filed: Dec. 22, 2009

(65) Prior Publication Data
US 2011/0146407 A1    Jun. 23, 2011

(51) Int. Cl.
*G01H 1/00* (2006.01)
(52) U.S. Cl. ......................................... 73/579
(58) Field of Classification Search .................. 73/579
See application file for complete search history.

(56) References Cited

U.S. PATENT DOCUMENTS

| | | | |
|---|---|---|---|
| 3,895,685 A * | 7/1975 | Gillette et al. ............... 181/0.5 |
| 4,393,711 A * | 7/1983 | Lapides ........................ 73/592 |
| 4,480,475 A * | 11/1984 | Tsao et al. .................... 73/610 |
| 4,685,334 A * | 8/1987 | Latimer ......................... 73/599 |
| 7,004,370 B2 * | 2/2006 | Arndt et al. ..................... 228/8 |
| 7,093,490 B2 * | 8/2006 | Kono et al. .................... 73/602 |
| 7,938,007 B2 * | 5/2011 | Huebler et al. ................ 73/622 |
| 2006/0137451 A1 * | 6/2006 | Dewangan et al. ........... 73/579 |
| 2009/0114021 A1 * | 5/2009 | den Boer ....................... 73/596 |

* cited by examiner

*Primary Examiner* — Hezron E Williams
*Assistant Examiner* — Rodney T Frank
(74) *Attorney, Agent, or Firm* — Mark E. Fejer

(57) ABSTRACT

A method for characterizing a defect of a defective heat fusion joint connecting two pipe segments in which the time of flight of an ultrasonic waveform reflected off an exterior surface of a heat fusion joint fitting connecting the two pipe segments or reflected off an interior wall of one of the pipe segments at a plurality of locations around the circumference of the heat fusion joint fitting is measured to determine the minimum and maximum times of flight, which correspond to the maximum and minimum combined wall thicknesses of the heat fusion joint fitting connecting the pipe segments and the pipe segment wall. If the difference between the minimum and maximum combined wall thicknesses as determined from the measured times of flight is equal to or greater than a predetermined amount, then the heat fusion joint is defective and possibly unacceptable for use, requiring a second set of time-of-flight measurements to characterize the nature of the defect.

14 Claims, 7 Drawing Sheets

METHOD FOR IDENTIFYING DEFECTIVE HEAT FUSION JOINTS

The U.S. Government has a paid-up license in this invention and the right in limited circumstance to require the patent owner to license others on reasonable terms as provided for by the terms of Contract No. DTPH56-07-T-000001 awarded by the U.S. Department of Transportation.

BACKGROUND OF THE INVENTION

1. Field of the Invention

This invention relates to a method for identifying defective heat fusion joints connecting two pipe segments from outside of the fitting. This invention further relates to the use of acoustic signals for identifying defective heat fusion joints. In one aspect, this invention relates to an acoustic method for measuring the ovality of a pipe segment connected with a heat fusion joint fitting. In one aspect, this invention relates to an acoustic method for measuring the angle of insertion of a pipe segment in a heat fusion joint fitting.

2. Description of Related Art

Plastic pipe segments are typically joined together by fusion joints. Such joints are made by heating the outside of a plastic pipe end and the inside of a plastic pipe fitting, e.g. coupling or tee, pushing the heated plastic pipe end into the heated fitting and allowing the resulting joint to cool. Electrofusion couplings are preassembled and then heated with wires embedded in the electrofusion coupling. A proper fusion joint is one where the pipe and the fitting are aligned along a common axis, i.e. coaxial alignment, and the pipe segment is substantially round. However, sometimes the pipe is inserted into the fitting at an angle and sometimes the pipe has an unacceptable amount of ovality which precludes the desired quality of joining around the periphery of the plastic pipe. To date, it has not been possible to "see" through the fitting and pipe to determine if either of these undesirable conditions exist after the joint is complete.

Ovality is defined as the difference between the largest diameter (semi-major axis) and smallest diameter (semi-minor axis) of a pipe divided by the average diameter times 100%. Testing has shown that poor quality joints result if the pipe ovality exceeds about 5%. Currently, there is a standard in place that requires ovality to be no more than 5% and pipes having an ovality which exceeds this amount are not to be used in a fusion joint. There is no standard specifying the maximum angle at which a pipe may be inserted into a fitting and still be acceptable. However, it is known that too large an angle can result in failure of the joint.

Conventionally, the ovality of a plastic pipe is measured by calipers on the outside of the pipe before the joint is formed. If the measured ovality exceeds 5%, then the joint should not be made. However, it is not now possible to determine the ovality of the pipe by mechanical means after the joint has been made. The angle the pipe makes with the fitting can be measured mechanically after the joint is formed. However, the same tightly confined spaces that led to the excessive angle also make it difficult to make this measurement.

SUMMARY OF THE INVENTION

Accordingly, it is one object of this invention to provide a method for identifying defective heat fusion joints. As used herein, a defective heat fusion joint is one in which at least one of the conditions of ovality and non-coaxial alignment is determined to exist in accordance with the method of this invention. However, depending upon the extent of the defect or defects, a defective heat fusion joint as defined herein may still be acceptable for use.

It is another object of this invention to provide a method for determining both the ovality and angle of pipe insertion into a heat fusion joint fitting after formation of the fusion joint as part of the inspection process assessing joint quality.

It is yet another object of this invention to provide a method for identifying defective heat fusion joints which are unacceptable for use.

These and other objects of this invention may be addressed by a method in which an acoustic waveform is applied to an exterior surface of a heat fusion joint fitting at a plurality of locations over substantially the entire circumference at a first circumferential location of the heat fusion joint fitting disposed around a pipe segment or applied to an interior surface of the pipe segment disposed within the heat fusion joint fitting. The time of flight of a reflected waveform reflected from the interior pipe wall of the pipe segment or the exterior surface of the heat fusion joint fitting is measured at each of the locations and a difference between an initial measured minimum time of flight and an initial measured maximum time of flight is determined, the initial measured minimum time of flight corresponding to a minimum combined wall thickness of the heat fusion joint fitting and the pipe segment, and the initial measured maximum time of flight corresponding to a maximum combined wall thickness of the heat fusion joint fitting and the pipe segment. The difference between the initial measured minimum time of flight and the initial measured maximum time of flight is then determined and compared with a predetermined difference between an initial measured minimum and an initial measured maximum corresponding to an acceptable heat fusion joint, resulting in a determination regarding the acceptability of the heat fusion joint, i.e. acceptable for use or defective and possibly not acceptable for use. The predetermined difference, and differences greater than the predetermined difference, represent values at which the heat fusion joint may be unacceptable. Depending on the outcome of the initial time-of-flight measurements, a second measurement may required in order to determine the nature of a measured defect, i.e. pipe ovality or angle of insertion.

BRIEF DESCRIPTION OF THE DRAWINGS

These and other objects and features of this invention will be better understood from the following detailed description taken in conjunction with the drawings, wherein.

DETAILED DESCRIPTION OF THE PRESENTLY PREFERRED EMBODIMENTS

Figure 3:
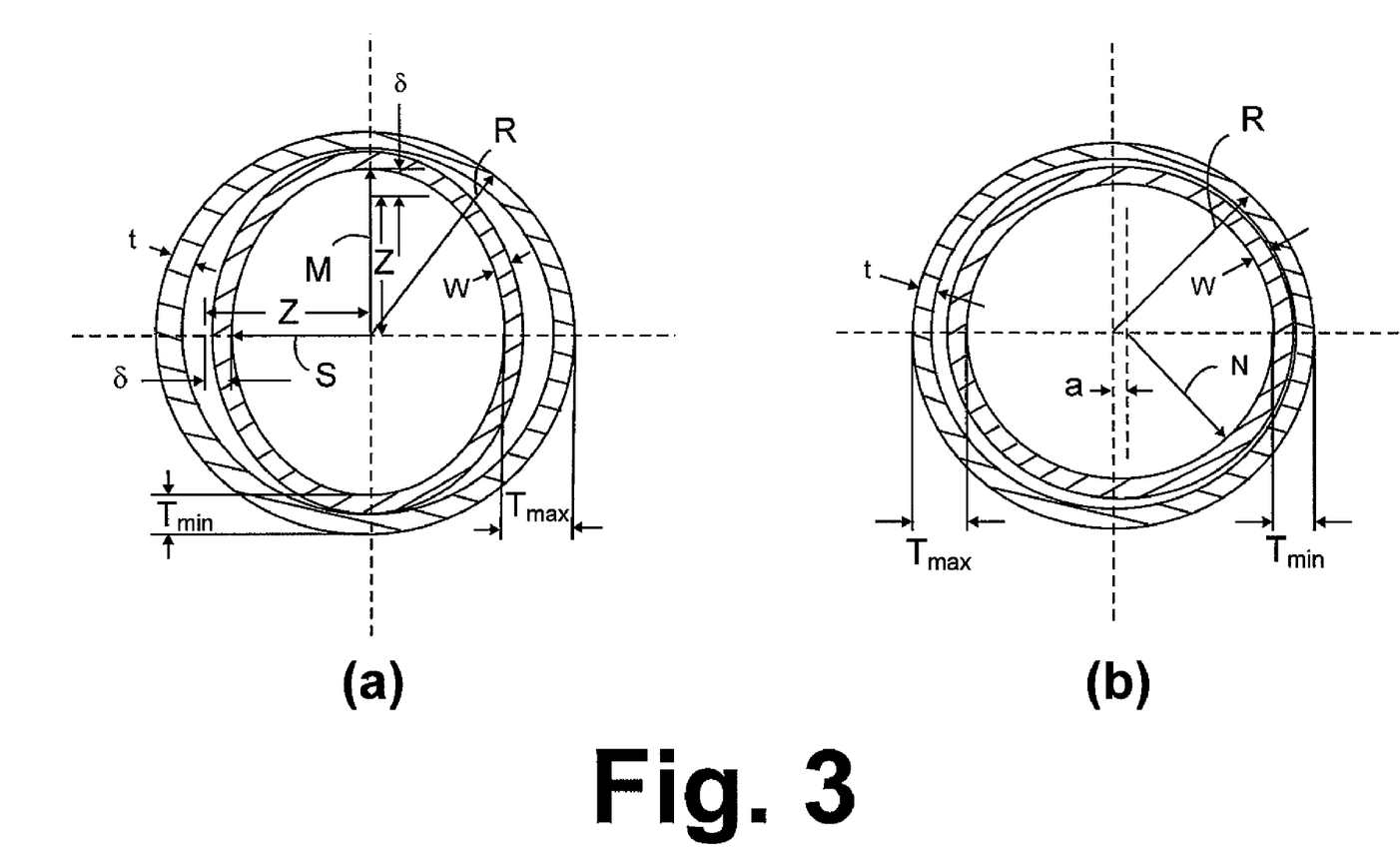
FIG. 3 is a schematic diagram showing the elements for characterizing the ovality and coaxial alignment of a heat fusion joint in accordance with the method of this invention.

The method of this invention measures the ovality and/or angle of insertion of a pipe segment in a heat fused plastic pipe joint from outside the heat fusion joint fitting with which the pipe segment is joined, where ovality of the pipe segment is defined by the equation $$Q = \frac{2(M-S)}{M+S+2W}$$

where M is the semi-major axis of the oval pipe, S is the semi-minor axis of the oval pipe, W is the thickness of the wall of the oval pipe, and Q is the ovality of the oval pipe (FIG. 3). This method may be used on joints made with socket fusion couplings, socket fusion tees, and electrofusion couplings, collectively referred to as fittings. Acoustic measurements are made around the circumference of the fitting from which the combined thickness of the fitting and pipe walls may be determined at each point on the circumference. The acoustic measurements may be made from inside the pipe segment or from outside the heat fusion joint fitting. We have found that a pipe that is oval or inserted at an angle produces a characteristic acoustic waveform time-of-flight pattern which may be used to reject a poor quality heat fusion joint. For example, a heat fusion joint in which an oval pipe segment coaxially aligned with the heat fusion joint fitting is disposed within the heat fusion joint fitting will produce a pattern of combined wall thickness measurements comprising two equal combined maximum thicknesses and two equal combined minimum thicknesses, as shown in FIG. 3(*a*), from which the ovality value can be determined. The ovality value can then be determined based upon the calculation of the difference between the combined minimum and combined maximum wall thicknesses.

FIG. 3(*a*) is a cross-sectional view of an oval pipe segment coaxially disposed within a substantially round heat fusion joint fitting which, upon application of an acoustic wave form to the exterior surface of the heat fusion joint fitting, will result in a measurement of two equal maximum and two equal minimum combined wall thicknesses. For a pure ovality defect, the minimum combined wall thickness is defined by the equation $$T_{min} = R - M$$

and the maximum combined wall thickness is $$T_{max} = R - S$$

where R is the outside radius of the heat fusion joint fitting. Accordingly, $$T_{max} - T_{min} = \frac{2Q(M+W)}{2+Q}$$

Assuming that the dimensional change ($\delta$) of the semi-major axis, M, and the semi-minor axis, S, are equal in magnitude, $T_{max} - T_{min}$ can be related to the radius of the pipe as follows:

$$\frac{[(W+M)-(S+W)]}{\frac{[(W+M)+(S+W)]}{2}} = Q = \frac{2[(Z+\delta+W)-(Z-\delta+W)]}{(Z+\delta+W)+(Z-\delta+W)}$$

where Z is the outside radius of the pipe. Thus, $$M = Z + \delta$$
$$S = Z - \delta$$

and $$\delta = \frac{Q}{2}(Z+W)$$

Accordingly, $$T_{max} - T_{min} = \frac{2Q(M+W)}{2+Q} = \frac{2Q(Z+\delta+W)}{2+Q}$$

which may be reduced to $$T_{max} - T_{min} = Q(Z+W) = QR_p$$

where $R_p$ is the outside radius of the pipe. Thus, for a value of Q greater than 0.05, i.e. 5%, the ovality of the pipe segment is deemed to be unacceptable and the heat fusion joint must be rejected.

Heat fusion joints in which the time-of-flight measurements of the acoustic waveform produce only one combined maximum wall thickness or one combined minimum wall thickness are joints in which the pipe segment has been inserted into the heat fusion joint fitting so as to result in a non-coaxial alignment with the heat fusion joint fitting. Such non-coaxial alignment may be due to insertion of the pipe segment at an angle into the heat fusion joint fitting, insertion of the pipe segment off center with respect to the heat fusion joint fitting, or a combination thereof. It will be appreciated that in addition to a non-coaxial alignment, the pipe segment may have some ovality and, because there is a standard for unacceptable ovality and no standard for unacceptable non-coaxial alignment, it is necessary to be able to determine the existence of ovality and, in the case in which ovality is determined to exist, the ovality value to determine whether the ovality is within acceptable limits, i.e. less than 5%. In those instances of a round, coaxially inserted pipe segment, the combined wall thickness will be substantially uniform around the entire circumference of the heat fusion joint.

Accordingly, in those instances in which the time-of-flight measurements result in only one combined maximum wall thickness or one combined minimum wall thickness, an additional measurement is required in order to determine whether the pattern is due solely to the non-coaxial insertion of the pipe segment into the heat fusion joint fitting or to a combination of pipe ovality and non-coaxial insertion. If yet a more detailed analysis is desired, equations describing elliptical conic sections can be curve fit to the data to yield the non-coaxial insertion and the amount of ovality.

Figure 1:
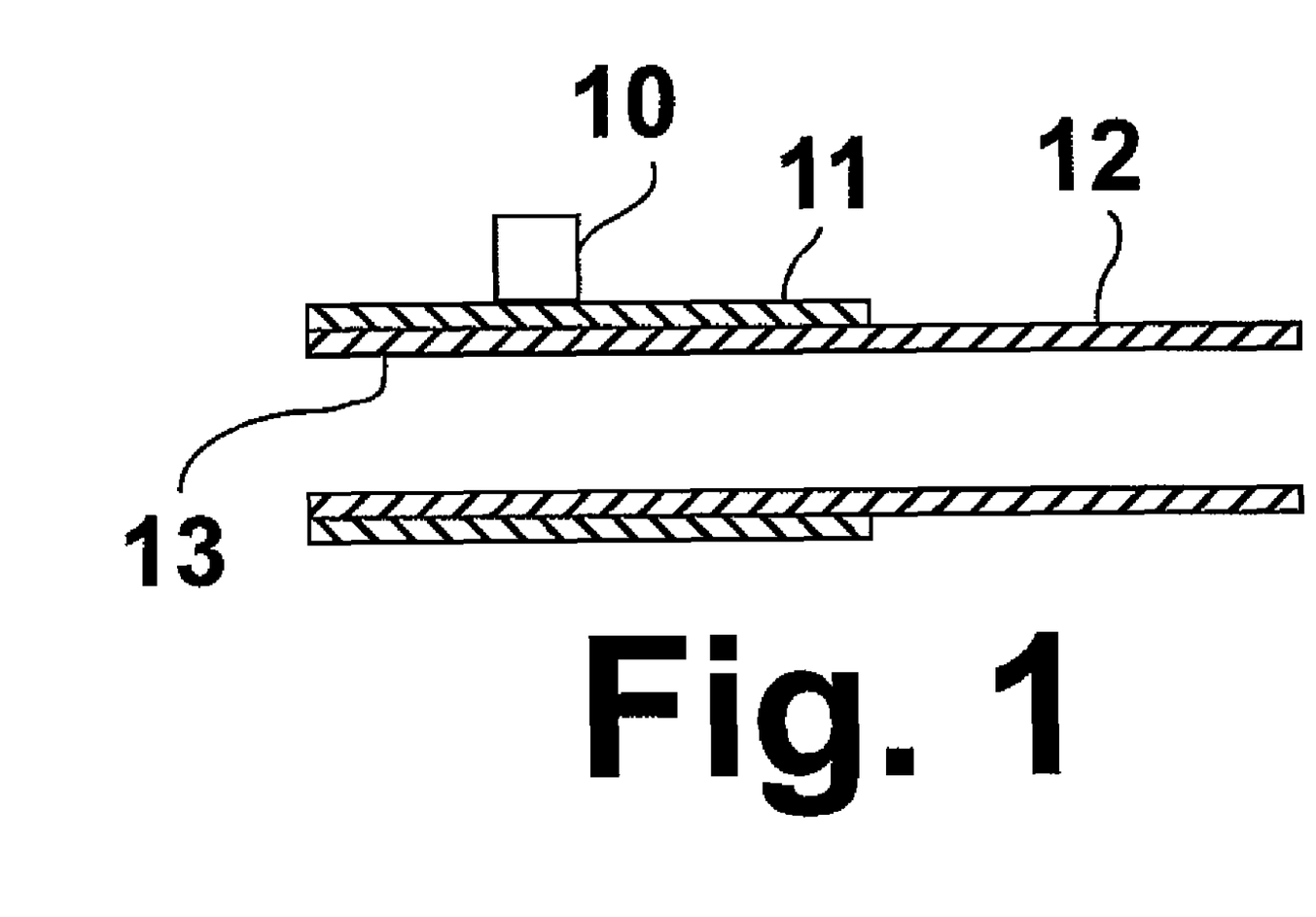
FIG. 1 is a schematic diagram showing the basic components of a mechanical setup for performing the method of this invention.

The first step in accordance with one embodiment of the method of this invention for characterizing a defect of a defective heat fusion joint connecting two pipe segments is the application to an exterior surface of the heat fusion joint fitting of an acoustic waveform at a plurality of locations over at least about 270 degrees, and preferably substantially 360 degrees, of the circumference of the heat fusion joint fitting at a first circumferential location of a heat fusion joint fitting disposed around a pipe segment. FIG. 1 shows the basic components required for the performance of this step. As shown therein, the acoustic waveform is applied by an acoustic transceiver (combined transmitter and detector) 10 disposed on the exterior surface of a fitting 11 disposed around a pipe segment 12. The acoustic transceiver is connected with a time-of-flight analyzer (not shown) which measures the time required for a waveform to travel from the acoustic transceiver through the wall of the fitting 11 and the wall of the pipe segment 12, reflect off the interior boundary 13 of the pipe wall, and return to the acoustic transceiver. In accordance with this embodiment, the transmitter and detector are in a pulse/echo arrangement. Although less desirable, the method of this invention may be carried out with an acoustic transmitter and separate acoustic signal detector disposed in a pitch/catch arrangement, where the acoustic waveform is "pitched" by the transmitter and "caught" by the detector.

In accordance with one particularly preferred embodiment, the acoustic waveform is generated by an ultrasonic acoustic transmitter. In accordance with a particularly preferred embodiment, the acoustic waveform has a frequency in the range of about 1 MHz to about 5 MHz. Upon detection of the reflected acoustic waveform, the time of flight of the waveform is determined at each location to which the acoustic waveform is applied and the minimum and maximum times of flight determined. If the difference between the minimum and maximum times of flight exceeds a certain predetermined value, then further testing is required to determine the reason for the difference, i.e. pipe ovality and/or angle of insertion. If there is no significant difference between the minimum and maximum measured times of flight, the fusion joint is acceptable with respect to ovality and coaxial alignment and no further testing is required. It will be appreciated that there may be other reasons or defects which may not be captured by the method of this invention which may result in an unacceptable heat fusion joint.

Figure 2:
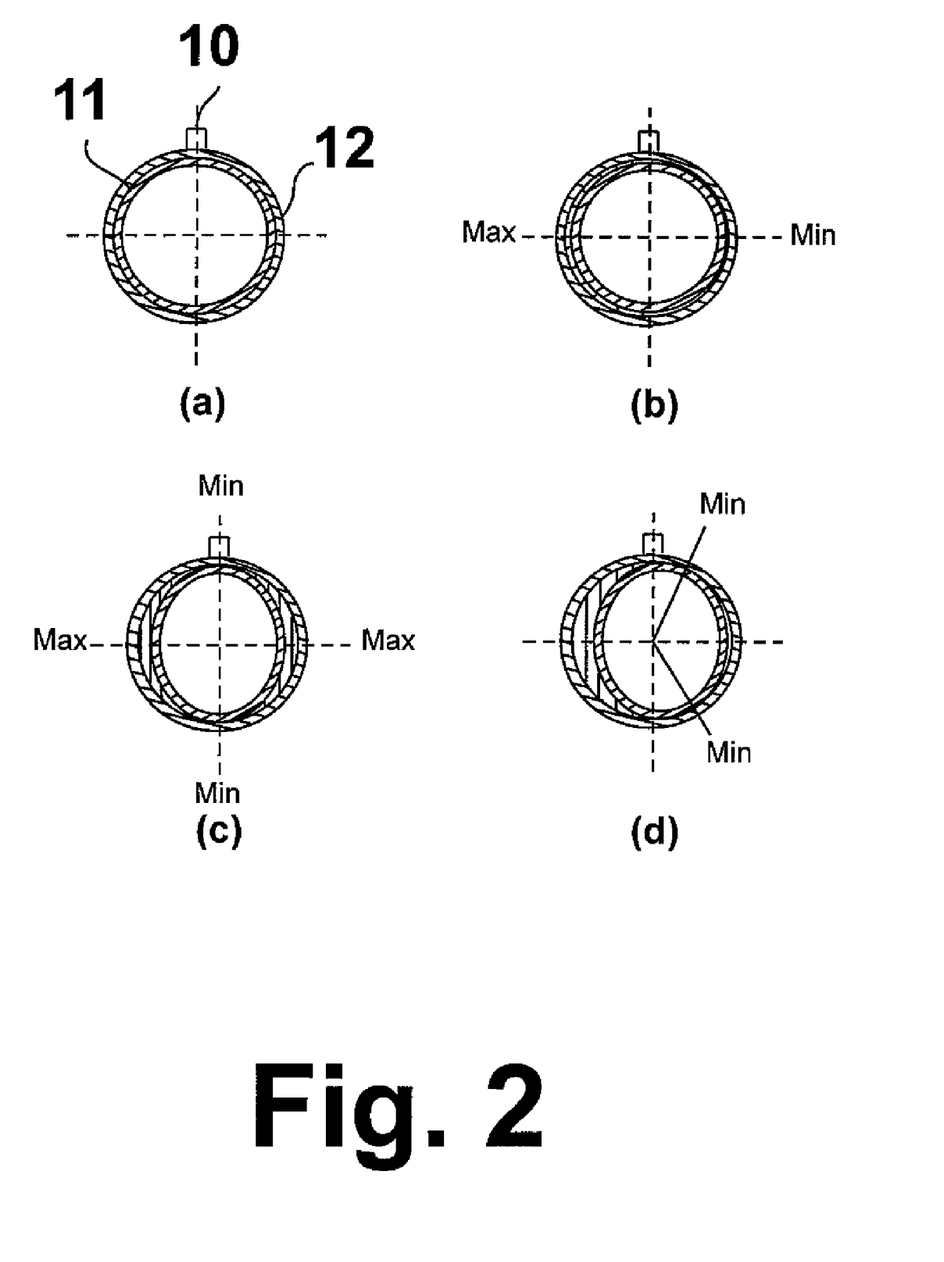
FIG. 2 is a radial cross-sectional diagram of various configurations of a pipe segment disposed within a heat fusion joint fitting to which the method of this invention may be applied.

FIG. 2 shows four different heat fusion joints which are characterized by the method of this invention. FIG. 2(a) is a heat fusion joint in which both the fitting 11 and the pipe segment 12 are round and the fitting and the pipe segment are concentrically disposed. FIG. 2(b) is a heat fusion joint in which both the fitting and the pipe segment are round, but the pipe segment is off-set, i.e. non-coaxially aligned, which may be representative of a pipe segment which is disposed in the fitting at an angle. FIG. 2(c) is a heat fusion joint in which the pipe segment is oval and coaxially disposed within the fitting. FIG. 2(d) is a heat fusion joint in which not only is the pipe segment oval, but also the pipe segment is off-set, i.e. disposed in the fitting at an angle. It is to be understood that the area between the exterior surface of the pipe segment and the interior surface of the heat fusion joint fitting is normally filled with material from the pipe segment and/or the heat fusion joint fitting, providing a continuous path for transmission of the acoustic waveform between the exterior surface of the heat fusion joint fitting and the interior wall of the pipe segment.

To be an acceptable heat fusion joint, the variation in the time of flight of the acoustic waveform based on a scan of at least 270 degrees of the circumference of the fitting must result in a pipe segment ovality of less than about 5%. It will be appreciated that when the heat fusion joint is as shown in FIG. 2(a), where the combined thickness of the fitting wall and the pipe segment wall is substantially uniform, the variation in the time of flight should be minimal. It will also be appreciated, as previously indicated, that even if the pipe segment ovality value is less than 5% and the pipe segment is coaxially aligned within the heat fusion joint fitting, the heat fusion joint may still be unacceptable for other reasons.

Figure 5:
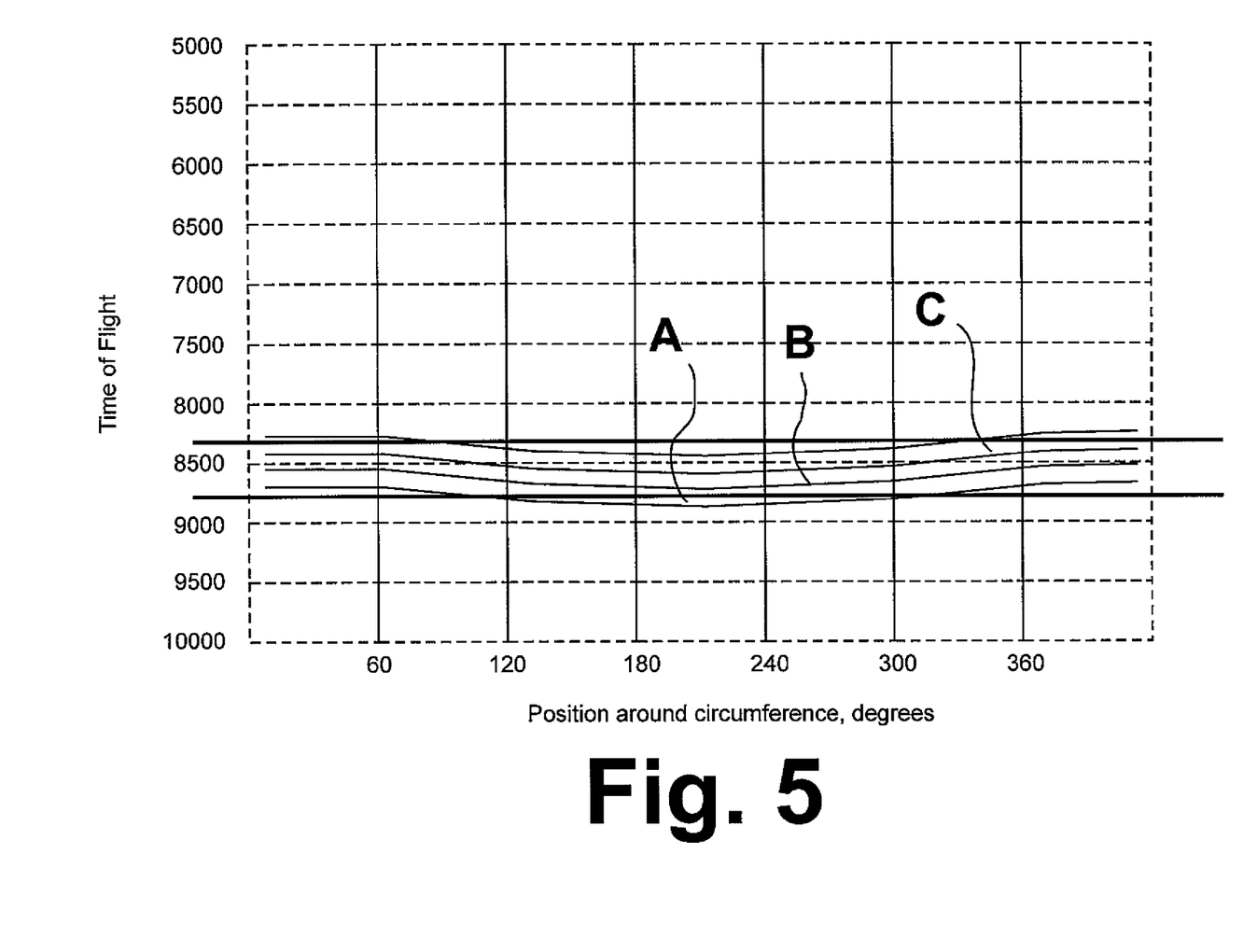
FIG. 5 is a diagram showing time-of-flight measurements resulting from a B-scan collected around the circumference of a 2-inch fusion coupling in accordance with one embodiment of the method of this invention.

FIG. 5 is a diagrammatic representation of the results of a B-scan ultrasound collected around the circumference of a 2-inch fusion coupling in accordance with one embodiment of this invention. A B-scan ultrasound is a two-dimensional display of sound waves reflected off the inner boundary of the pipe segment wall. In FIG. 5, the horizontal axis provides the position of the acoustic sensor or detector on the circumference and the vertical axis is proportional to the time required for a wave reflection from a flaw or boundary in the fitting/pipe segment. Signals between 0 and 4500 on the vertical axis are not shown because they do not assess fusion quality. The lines A, B, and C represent peaks and valleys in the waveforms reflecting from the interior pipe wall. If the pipe were centered in the fitting and had 0% ovality, i.e. no ovality, the lines between 8500 and 8700 would be flat. The fact that the lines are not flat indicates that the pipe segment is either oval, inserted at an angle or otherwise non-coaxially aligned, or both. To determine which of these conditions exists requires a second circumferential scan, which is performed at a second circumferential location spaced apart from the first circumferential location. However, as previously indicated, a pipe segment that is oval and co-axially inserted in the heat fusion joint fitting or a pipe segment that is round and co-axially inserted in the heat fusion joint fitting can be determined with a single circumferential scan.

Figure 4:
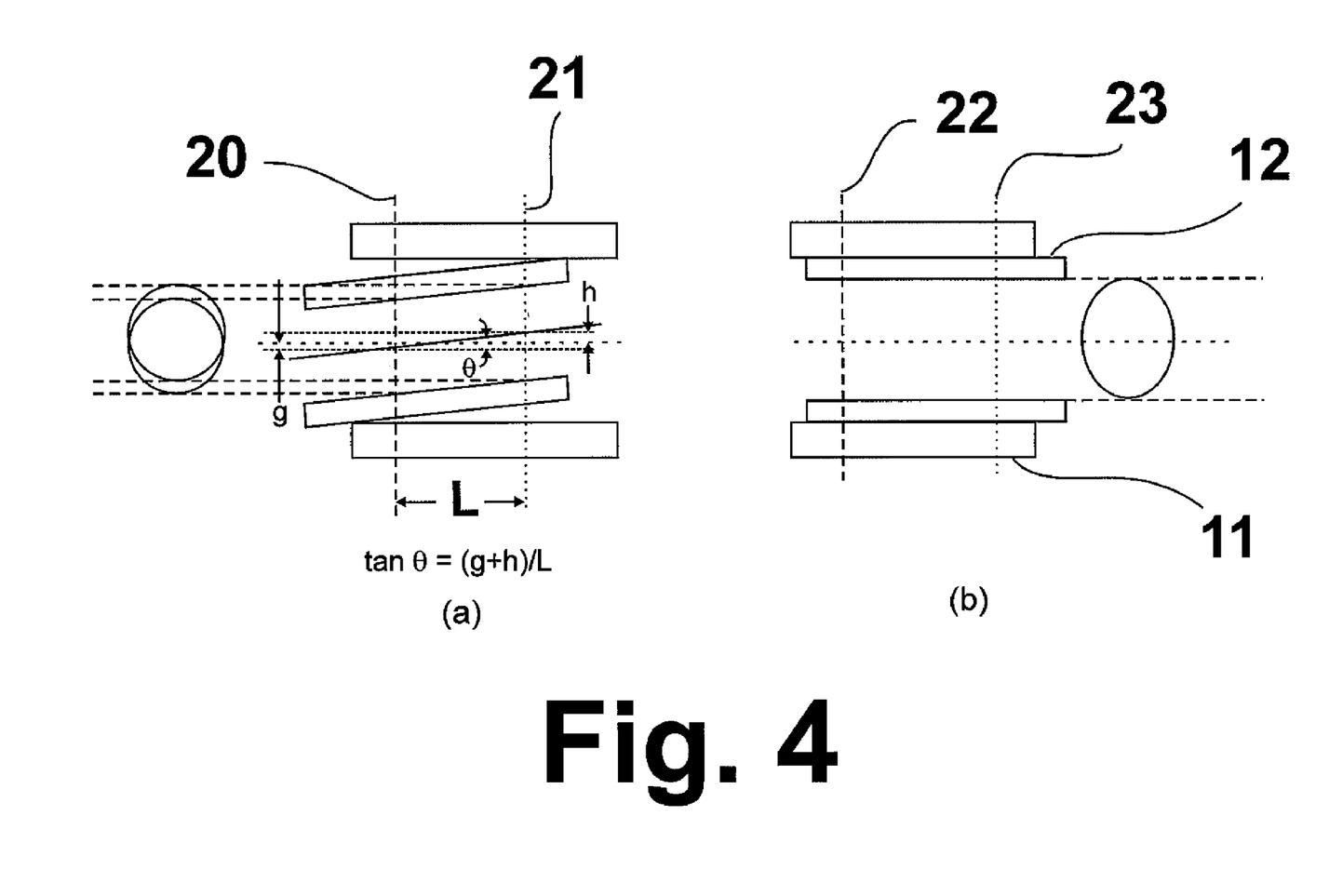
FIG. 4 is a diagrammatic representation showing the results of locations and circumferential scans of a fusion joint from which a determination can be made that the pipe is non-coaxially aligned, oval, or both in accordance with one embodiment of the method of this invention.

FIG. 4 shows the results obtainable from a second circumferential scan from which a determination can be made as to the type of defect. The dotted lines 20, 21 and 22, 23 show the positions for the two circumferential scans. If, as illustrated in FIG. 4(b), the pipe were oval, the scans at the two circumferential locations 22, 23 would show the same time-of-flight maximums and minimums at the same corresponding locations on the circumference of the fitting. If, as illustrated FIG. 4(a), the pipe were at an angle, the maximum and minimums would reverse, the thickest measurement occurring along the circumference represented by dotted line 21 and the thinnest measurement occurring along the circumference represented by dotted line 20. For the situation in which a circular pipe segment is inserted at an angle into a heat fusion joint fitting and for two circumferential scans taken at a distance, L, apart as shown in FIG. 4(a), the center of the radial cross-section of the pipe segment at one of the scan locations 20 will be offset from the axis of the heat fusion joint fitting by an amount g and the center at the other scan location 21 will be offset by an amount h. In this case as shown in FIG. 3(b), $$T_{max} = R - (N + a) = R - N + a$$

$$T_{min} = R - (N - a) = R - N - a$$

$$T_{max} - T_{min} = 2a$$

$$a = \frac{T_{max} - T_{min}}{2}$$

Thus, the angle of insertion may be determined as follows $$\tan\theta = \left[\frac{(T_{max} - T_{min})_{scan1}}{2} + \frac{(T_{max} - T_{min})_{scan2}}{2}\right] / L$$

Figure 6:
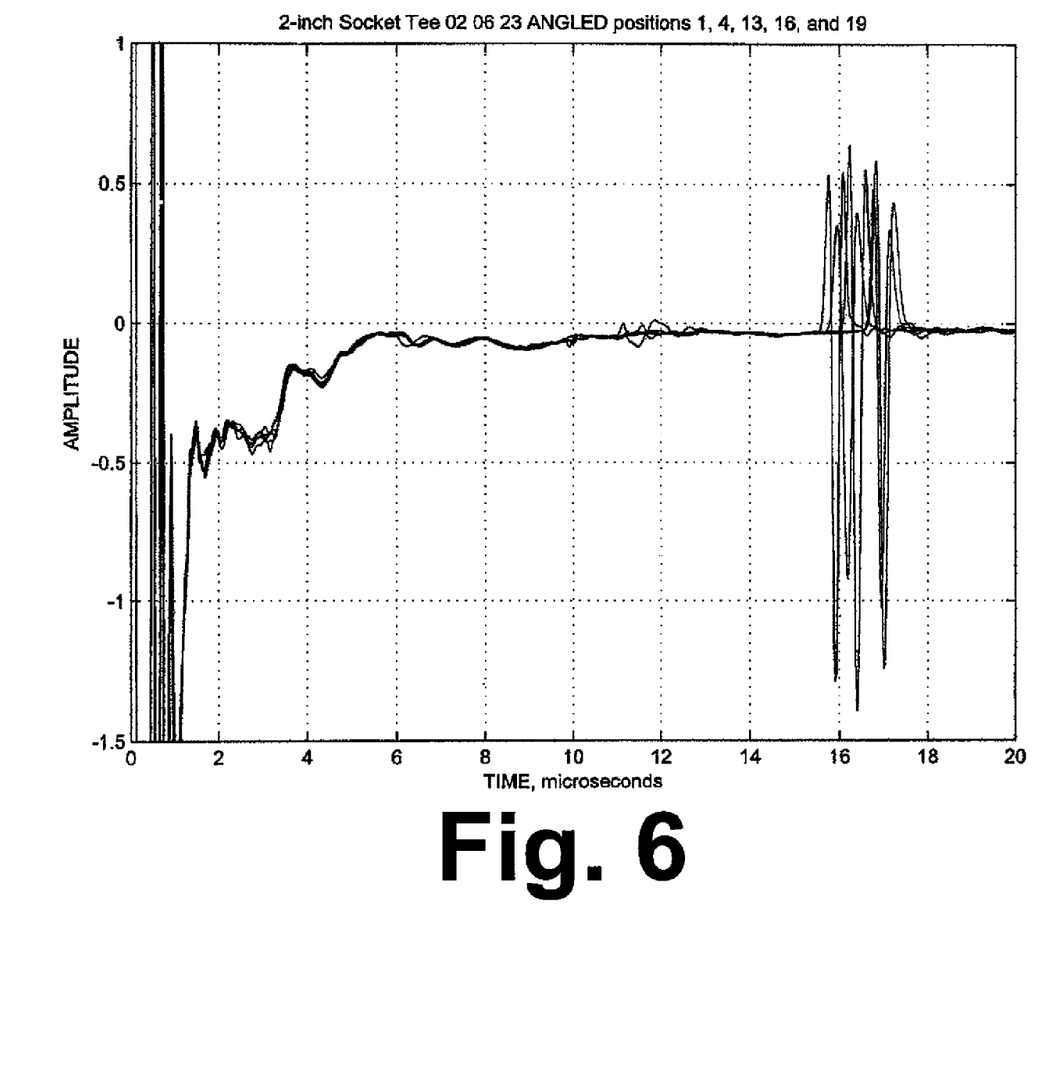
FIG. 6 is a diagram showing reflection times for an acoustic waveform from the inner pipe wall of a heat fusion joint at various locations on the circumference of the heat fusion joint fitting.
Figure 7:
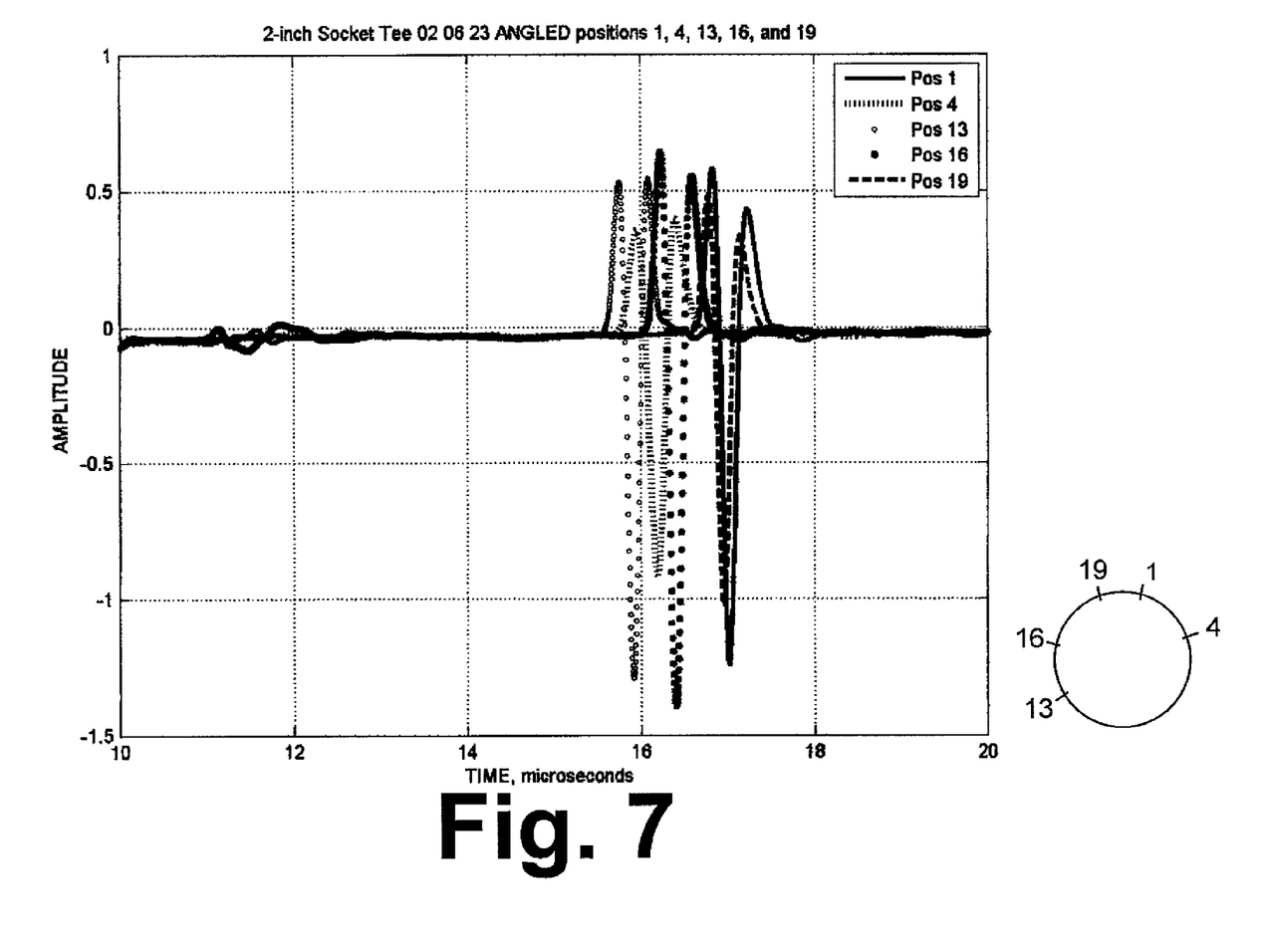
FIG. 7 is an amplified view of the diagram of FIG. 6 showing details of the reflection times for an acoustic waveform from the inner pipe wall of a fusion joint at various locations on the circumference of the heat fusion fitting.

FIG. 6 shows reflection times for an acoustic waveform from the inner pipe wall of a fusion joint at various locations on the circumference of a heat fusion fitting. As can be seen, there is a spread in reflection times from the inner pipe wall at about 16 to 18 microseconds. FIG. 7 shows an amplified view of the reflection times shown in FIG. 6 so as to more clearly illustrate the reflection times corresponding to each position (1, 4, 13, 16, and 19) on the circumference of the fitting.

It will be appreciated by those versed in the art that, while a 360 degree scan of the circumferential locations is not required, there is a minimum distance around the circumferential location, i.e. 270 degrees, to which the acoustic waveform must be applied to ensure measurement of both the minimum and maximum times of flight for the waveform. In addition, the maximum distance between locations on the circumference of the fitting at which the acoustic waveform is applied and the time-of-flight measurements are made is about 45 degrees of the circumference. The use of distances greater than about 45 degrees of the circumference provides a possibility that the maximum and/or minimum times of flight will not be obtained. In accordance with one preferred embodiment, the distance between locations is about 30 degrees of the circumference. Although not required, in accordance with one preferred embodiment of this invention, the locations on the circumference of the fitting at which the acoustic waveform is applied and the time-of-flight measurements are made are evenly spaced apart. In addition, the acoustic waveform is applied as pulses at each of the locations on the circumference. If a more detailed analysis using conic sections is desired, enough measurements must be taken to enable proper curve fitting.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for determining a presence of and characterizing a defect of a heat fusion joint connecting two pipe segments comprising the steps of:
    applying an acoustic waveform at a plurality of locations over at least 270 degrees of a circumference of a heat fusion joint fitting disposed around a pipe segment to one of an exterior surface of said heat fusion joint fitting and an interior surface of said pipe segment;
    measuring a time of flight of a reflected waveform reflected from one of an interior pipe wall of said pipe segment and said exterior surface of said heat fusion joint fitting at each of said locations;
    determining each measured minimum time-of-flight location on said circumference and each measured maximum time-of-flight location on said circumference; and
    determining from each said measured minimum time-of-flight location and each said measured maximum time-of-flight location whether or not said heat fusion joint is a defective heat fusion joint.

2. The method of claim 1, wherein a second acoustic waveform is applied at a plurality of additional locations over said at least 270 degrees of said circumference at a second circumferential location of said heat fusion joint fitting having said defective heat fusion joint, said second circumferential location spaced apart from said first circumferential location, measuring an additional time of flight of an additional reflected waveform reflected from said one of said interior pipe wall of said pipe segment and said exterior surface of said heat fusion joint fitting at each of said additional locations, determining each additional measured minimum and each additional measured maximum of said time flight for said second circumferential location, one of comparing each said additional measured minimum with each said measured minimum and comparing each said additional measured maximum with each said measured maximum, and identifying a defect of said defective heat fusion joint selected from the group consisting of pipe segment ovality and pipe segment non-coaxial alignment within said heat fusion joint fitting based on said comparisons, wherein substantially identical measured minimums and substantially identical measured maximums correspond to an ovality defect and different measured minimums and different measured maximums correspond to a non-coaxial aligned pipe segment.

3. The method of claim 1, wherein a difference between said time of flight at each said measured minimum time-of-flight location and at each said measured maximum time-of-flight location is determined, producing an acceptability factor, and wherein said acceptability factor is compared with a predetermined acceptability factor limit, thereby enabling determination of an acceptability of the heat fusion joint at least with respect to ovality.

4. The method of claim 1, wherein said acoustic waveform is an ultrasonic waveform.

5. The method of claim 4, wherein said ultrasonic waveform has a frequency in a range of about 1 MHz to about 5 MHz.

6. The method of claim 1, wherein a transmitter of said acoustic waveform and a detector of said reflected waveform are in a pulse/echo relationship.

7. The method of claim 1, wherein said locations are substantially evenly spaced apart.

8. The method of claim 7, wherein said locations are spaced apart by no more than about 45 degrees of said circumference.

9. The method of claim 8, wherein said locations are spaced apart by no more than about 30 degrees of said circumference.

10. The method of claim 1, wherein said acoustic waveform is applied as pulses at said locations.

11. The method of claim 1, wherein said acoustic waveform is applied in pulses over substantially 360 degrees of said circumference.

12. A method for identifying defective heat fusion joints of pipe segments joined by a heat fusion fitting comprising the steps of:
    performing a B-scan ultrasound around at least 270 degrees of a circumference of a heat fusion joint fitting connecting two pipe segments disposed at a first circumferential location from one of an exterior of said heat fusion joint fitting and an interior of one of said pipe segments;
    determining a combined thickness of a fitting wall and a pipe segment wall at a plurality of substantially evenly spaced apart locations of said circumference, said locations being spaced apart by less than about 45 degrees of said circumference; and
    determining a difference, if any, between a first minimum combined wall thickness and a first maximum combined wall thickness, whereby said difference corresponds to a defective heat fusion joint.

13. The method of claim 12 further comprising performing an additional B-scan ultrasound around at least 270 degrees of said circumference at a second circumferential location of said heat fusion joint fitting, determining a second combined thickness of said fitting wall and said pipe segment wall at a plurality of substantially evenly spaced apart locations of said circumference at said second circumferential location, said locations being spaced apart by less than about 45 degrees of said circumference, and comparing said first minimum combined wall thickness with a second minimum combined wall thickness determined from said additional B-scan ultrasound, whereby substantial identity of said minimum combined thicknesses corresponds to an ovality defect and a difference between said minimum combined thickness corresponds to a non-coaxially aligned pipe segment.

14. The method of claim 12, wherein a frequency of said B-scan ultrasound is in a range of about 1 Mhz to about 5 MHz.

* * * * *